United States Patent
Cha et al.

(10) Patent No.: US 11,640,099 B2
(45) Date of Patent: May 2, 2023

(54) HIGH TEMPERATURE HIGH PRESSURE (HTHP) CELL IN SUM FREQUENCY GENERATION (SFG) SPECTROSCOPY FOR LIQUID/LIQUID INTERFACE ANALYSIS

(71) Applicant: SAUDI ARABIAN OIL COMPANY, Dhahran (SA)

(72) Inventors: Dong Kyu Cha, Dhahran (SA); Mohammed Badri Alotaibi, Dhahran (SA); Salah H. Alsaleh, Dhahran (SA); Ali Abdallah Al-Yousef, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 423 days.

(21) Appl. No.: 16/787,849

(22) Filed: Feb. 11, 2020

(65) Prior Publication Data

US 2021/0247661 A1    Aug. 12, 2021

(51) Int. Cl.
*G01N 1/44*      (2006.01)
*G02F 1/35*      (2006.01)
(Continued)

(52) U.S. Cl.
CPC ............. *G02F 1/3534* (2013.01); *G01N 1/10* (2013.01); *G01N 1/44* (2013.01); *E21B 47/06* (2013.01); *G01N 2001/1062* (2013.01)

(58) Field of Classification Search
CPC .......... G02F 1/3534; G01N 1/10; G01N 1/44; E21B 47/06
(Continued)

(56) References Cited

U.S. PATENT DOCUMENTS

| 4,994,671 A | 2/1991 | Safinya et al. |
| 2003/0062472 A1 | 4/2003 | Mullins et al. |

(Continued)

FOREIGN PATENT DOCUMENTS

| CN | 1864066 A | 11/2006 |
| CN | 103334726 A | 10/2013 |

(Continued)

OTHER PUBLICATIONS

Sanchez, M. Alejandra et al., "Experimental and theoretical evidence for bilayer-bybilayer surface melting of crystalline ice" PNAS, 2017, 114 (2), pp. 227-232 (6 pages).

Dellwig, T. et al., "Bridging the Pressure and Materials Gaps: High Pressure Sum Frequency Generation Study on Supported Pd Nanoparticles" Physical Review Letters, 2000, 85 (4), pp. 776-779 (4 pages).

(Continued)

*Primary Examiner* — Robert R Raevis
(74) *Attorney, Agent, or Firm* — Osha Bergman Watanabe & Burton LLP (57) ABSTRACT

A pressure cell for sum frequency generation spectroscopy includes: a metal pressure chamber; a heating stage that heats the liquid sample; a pump, connected to an interior of the metal pressure chamber, that pressurizes the interior of the metal pressure chamber; and a controller that controls the pump and the heating stage to control a pressure of the interior of the metal pressure chamber and a temperature of a liquid sample. The metal pressure chamber includes: a base that retains the liquid sample; a removable lid that seals against the base to enclose the liquid sample in the metal pressure chamber; and a window in the removable lid that exposes the liquid sample to an exterior of the metal pressure chamber.

14 Claims, 10 Drawing Sheets

(51) Int. Cl.
    *G01N 1/10* (2006.01)
    *E21B 47/06* (2012.01)
(58) Field of Classification Search
    USPC ... 73/61.41–61.44, 61.48, 61.71, 64.56, 863,
        73/864.81, 866; 356/36, 300–334,
        356/335–343; 166/250.01; 250/306,
        250/440.11, 343–346, 341.1, 341.6, 341.8
    See application file for complete search history.

(56) References Cited

U.S. PATENT DOCUMENTS

| | | |
|---|---|---|
| 2004/0012844 A1 | 1/2004 | Ohtsuki et al. |
| 2009/0114805 A1 | 5/2009 | Csutak |
| 2011/0151576 A1 | 6/2011 | Perfect et al. |
| 2014/0273266 A1 | 9/2014 | Grindstaff et al. |
| 2015/0015937 A1 | 1/2015 | Vermeulen et al. |
| 2015/0096746 A1 | 4/2015 | DiFoggio et al. |
| 2016/0320686 A1 | 11/2016 | Hansen et al. |
| 2017/0314383 A1 | 11/2017 | Ispirescu et al. |
| 2018/0010992 A1 | 1/2018 | Gahlawat et al. |
| 2018/0180404 A1 | 6/2018 | Hunt et al. |
| 2018/0345236 A1 | 12/2018 | Noguchi et al. |

FOREIGN PATENT DOCUMENTS

| | | | |
|---|---|---|---|
| CN | 103712931 A | | 4/2014 |
| CN | 103940818 A | | 7/2014 |
| CN | 105626019 A | | 6/2016 |
| CN | 107219322 A | | 9/2017 |
| CN | 107703036 A | | 2/2018 |
| CN | 110132789 | * | 8/2019 |
| CN | 111213633 | * | 6/2020 |
| JP | 2004111444 | * | 4/2004 |
| JP | 2019113623 A | | 7/2019 |
| WO | 2018/231116 A1 | | 12/2018 |

OTHER PUBLICATIONS

Weber, Jan "Temperature induced change in aliphatic monolayers observed by vibrational sum-frequency generation spectroscopy" Dissertation, Universitat Duisburg-Essen, Aug. 2014 (110 pages).

Rupprechter, Günther "Sum Frequency Generation and Polarization-Modulation Infrared Reflection Absorption Spectroscopy of Functioning Model Catalysts from Ultrahigh Vacuum to Ambient Pressure" Institute of Materials Chemistry, Vienna University of Technology, Veterinärplatz 1, A-1210 Vienna, Adv. Catal. 51 (2007) 133-263 (131 pages).

Tutuncu, Azra N. and Robert Joha, "An Experimental Study for Removal of Near-Wellbore Asphaltene Deposits Using Ultrasonics", SEG Technical Program Expanded Abstracts 2008, Jan. 2008, pp. 1719-1723 (5 pages).

Alotaibi, M B et al., "Novel Characterization of Thin Film at Reservoir Fluids Interfaces in Carbonates", SPE-194757-MS, SPE Middle East Oil and Gas Show and Conference, Society of Petroleum Engineers, Mar. 2019, pp. 1-14 (14 pages).

International Search Report issued in related International Application No. PCT/US2020/021061, dated Oct. 15, 2020 (5 pages).

Written Opinion issued in related International Application No. PCT/US2020/021061, dated Oct. 15, 2020 (7 pages).

Somorjai, Gabor A. et al., "The evolution of model catalytic systems; studies of structure, bonding and dynamics from single crystal metal surfaces to nanoparticles, and from low pressure (<10-3 Torr) to high pressure (>10-3 Torr) to liquid interfaces", Physical Chemistry Chemical Physics, Owner Societies, vol. 9, 2007, pp. 3500-3513 (14 pages).

International Search Report issued in corresponding International Application No. PCT/US2020/020887, dated Oct. 15, 2020 (4 pages).

Written Opinion issued in corresponding International Application No. PCT/US2020/020887, dated Oct. 15, 2020 (8 pages).

* cited by examiner

HIGH TEMPERATURE HIGH PRESSURE (HTHP) CELL IN SUM FREQUENCY GENERATION (SFG) SPECTROSCOPY FOR LIQUID/LIQUID INTERFACE ANALYSIS

TECHNICAL FIELD

Embodiments described herein relate generally to apparatus, systems, and methods for performing sum frequency generation (SFG) spectroscopy under simulated conditions. More particularly, embodiments described herein relate to apparatus, systems, and methods for performing SFG spectroscopy of liquid hydrocarbon samples under simulated reservoir conditions.

BACKGROUND

Water injection is a common technique used in oil production to increase the yield of hydrocarbons from a reservoir. The interactions between the various phases in the reservoir (e.g., oil, water, brines, calcite rock, and gas) can greatly affect yield of the recovered hydrocarbons. For example, by controlling the salinity and the ionic strength of the injected solution, the wettability of rock formations in the reservoir can be changed to improve recovery. To further improve the yield of hydrocarbons, various spectroscopic techniques such as SFG spectroscopy have been used to understand the nature of the interactions between the phases in the reservoir and characterize the chemical and molecular structure and interfaces of the phases.

SUMMARY

In one aspect, one or more embodiments disclosed herein relate to a pressure cell for SFG spectroscopy. The pressure cell includes: a metal pressure chamber that includes a base that retains a liquid sample, a removable lid that seals against the base to enclose the liquid sample in the metal pressure chamber, and a window in the removable lid that exposes the liquid sample to an exterior of the metal pressure chamber; a heating stage that heats the liquid sample; a pump, connected to an interior of the metal pressure chamber, that pressurizes the interior of the metal pressure chamber; and a controller that controls the pump and the heating stage to control a pressure of the interior of the metal pressure chamber and a temperature of the liquid sample.

In another aspect, one or more embodiments disclosed herein relate to a system for performing SFG spectroscopy. The system includes: a pressure cell and a sum frequency generation microscope. The pressure cell includes: a metal pressure chamber including a base that retains a liquid sample, a removable lid that seals against the base to enclose the liquid sample in the metal pressure chamber, and a window in the removable lid that exposes the liquid sample to an exterior of the metal pressure chamber; a heating stage that heats the liquid sample; a pump, connected to an interior of the pressure chamber, that pressurizes the interior of the metal pressure chamber; and a controller that controls the pump and the heating stage to control a pressure of the interior of the metal pressure chamber and a temperature of the liquid sample. The sum frequency generation microscope includes: a first variable light source that generates light of a first frequency; a second light source that generates light of a second frequency; and a detector that detects light.

In another aspect, one or more embodiments disclosed herein relate to a method of performing SFG spectroscopy. The method includes: loading a liquid sample into a metal pressure chamber of the pressure cell, wherein the metal pressure chamber comprises a base and removeable lid; sealing the removable lid against the base to enclose the liquid sample in the metal pressure chamber; heating the liquid sample with a heating stage; pressurizing an interior of the metal pressure chamber with a pump that is connected to the interior of the metal pressure chamber; illuminating a surface of the liquid sample with light of a first frequency and light of a second frequency through a window of the metal pressure chamber; collecting, through the window, light of a third frequency from the surface of the liquid sample, wherein the third frequency is the sum of the first frequency and the second frequency.

Other aspects and advantages will be apparent from the following description and the appended claims.

DETAILED DESCRIPTION

Specific embodiments of the present disclosure will now be described in detail with reference to the accompanying figures. Like elements in the various figures are denoted by like reference numerals for consistency.

Numerous specific details are set forth in the following detailed description in order to provide a more thorough understanding of embodiments of the present disclosure. However, it will be apparent to one of ordinary skill in the art that the present disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create a particular ordering of the elements nor to limit any element to being only a single element unless expressly disclosed, such as by the use of the terms "before," "after," "single," and other such terminology. Rather the use of ordinal numbers is to distinguish between the elements. By way of an example, a first element is distinct from a second element, and the first element may encompass more than one element and succeed (or precede) the second element in an ordering of elements.

Figure 1A:
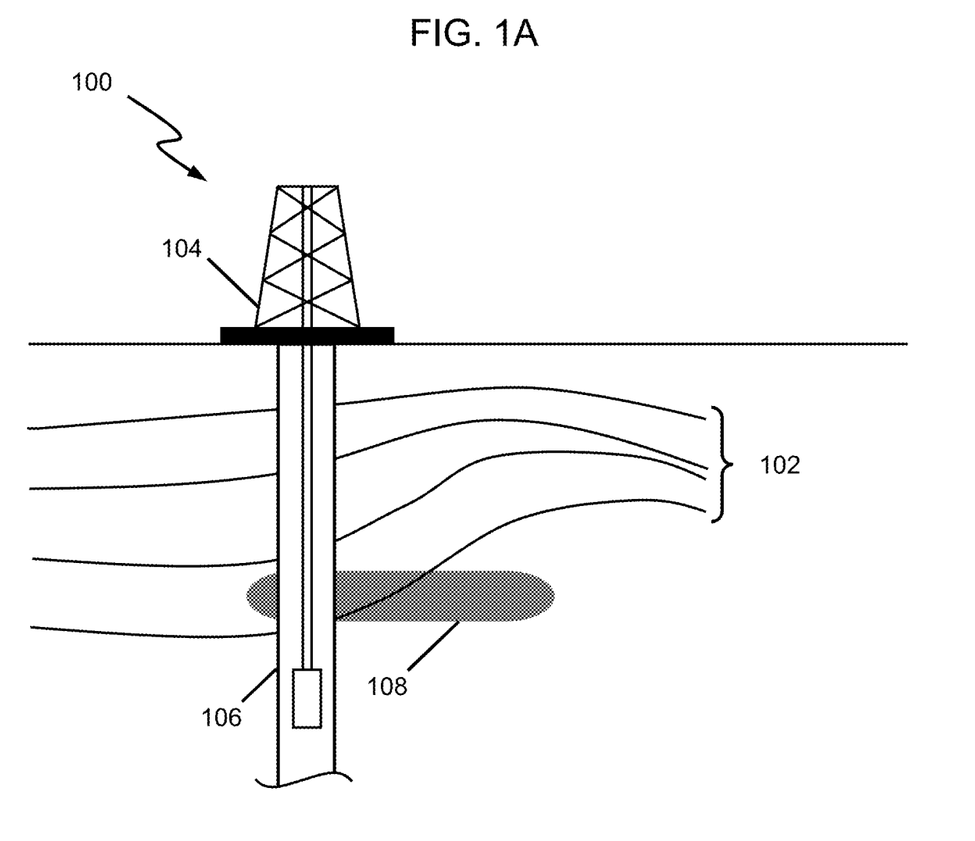
FIG. 1A shows an oil and gas production facility.

In general, embodiments disclosed herein provide an apparatus, a system, and a method for performing sum frequency generation (SFG) spectroscopy under simulated reservoir conditions to characterize the molecular and chemical structures and interfaces of a liquid sample. For example, as shown in FIG. 1, an oil production facility 100 located above a hydrocarbon reservoir 102 may include an oil rig 104 and an oil well 106 to extract hydrocarbons 108. The hydrocarbons 108 may be extracted by pressurizing the reservoir 102 with an injection solution (e.g., conventional water injection, specialized aqueous solution injection) from a second well (not shown).

To improve the effectiveness of the injection recovery technique, the microscopic characteristics of, and interactions between, the hydrocarbons 108, the injection solution, and the rock formations of the reservoir 102 may be studied. Examples of such interactions may include surface charge interaction, ionic exchange, and rock dissolution. SFG spectroscopy may be used to probe the fluid/fluid or fluid/rock interactions and to characterize the chemical and molecular structures and interfaces of a liquid sample, discussed in further detail below. Accordingly, one or more embodiments disclosed herein relate to an apparatus, a system, and a method of studying a liquid sample in a simulated high temperature and high pressure reservoir environment with SFG spectroscopy. Alternatively, other optical techniques (e.g., difference frequency generation (DFG) spectroscopy, Raman spectroscopy) may be used in conjunction with embodiments disclosed herein.

In one or more embodiments, a liquid sample may be extracted from a subsurface facility (e.g., the reservoir 102). For example, a live oil sample may be obtained from the oil well 106. Furthermore, to more closely recreate the actual fluids found downhole in the well, gases may be remixed (e.g., hydrocarbon gases, hydrogen sulfide, and the like) into the oil sample. The live oil composition may be previously determined using a modular formation dynamic tester (an MDT technique).

In one or more embodiments, the sample collected from the subsurface facility may be separated into two phases: an organic phase (i.e., primarily hydrocarbons 108) and the second component includes an aqueous phase (i.e., primarily water). Then, the two phases may be remixed with a predetermined ratio and/or predetermine level of emulsification. Thus, the liquid sample may be a synthetic brine, prepared in a laboratory, comprising the extracted hydrocarbons 108 and an aqueous solution.

The term "brine" is defined as a mixture comprising two or more immiscible liquids. A first component of the brine is dispersed in a second component of the brine. In one or more embodiments, the dispersed first component includes an organic phase (i.e., primarily hydrocarbons) and the second component includes an aqueous phase (i.e., primarily water). Alternatively, the phases of the first and second components may be reversed. In one or more embodiments, the liquid sample may be a brine comprising gaseous hydrocarbons, liquid hydrocarbons, solid hydrocarbons, salts, metals, impurities, water, an aqueous solution, and any combination thereof.

Figure 1B:
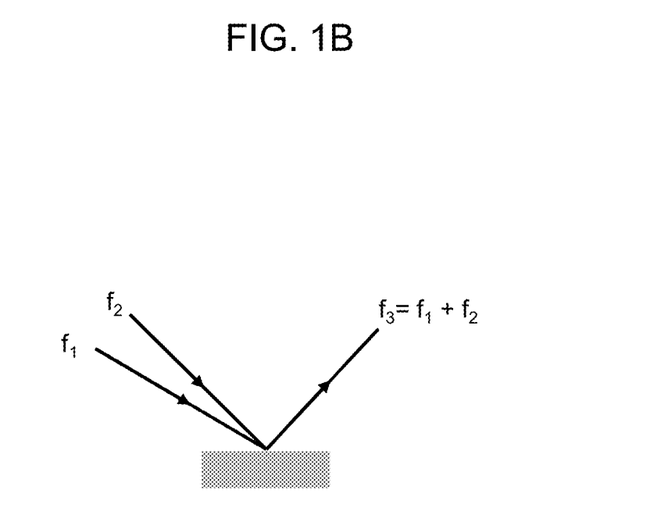
FIG. 1B shows a schematic of a sum frequency generation system.

FIG. 1B shows a schematic of a sum frequency generation system. In sum frequency generation, a sample is probed with two incident light beams that overlap in space (i.e., both beams converge at a point on the sample) and time (i.e., the pulses from both beams are incident on the sample at the same time). The first light beam is centered at a first frequency $f_1$ that may correspond with an energy level of a molecular vibrational mode that occurs in the sample (e.g., corresponds to an infrared wavelength of light). The first frequency may be continuously or discretely changed (e.g., with a tunable light source, a filtered light source, a spectrometer, or the like) to probe different energy levels of different molecular vibrational modes in the sample. The second light beam is centered at a second frequency $f_2$ that is different from the first frequency $f_1$ and may correspond to a virtual energy state (e.g., corresponds to a visible wavelength of light). After absorbing the two coincident light pulses, non-linear effects induced by the non-linear susceptibility of the sample causes the surface of the sample to emit light of a third frequency $f_3$ that is the sum of the first and second frequencies $f_1$, $f_2$ (i.e., an SFG signal).

In one or more embodiments, an SFG spectrum is generated by scanning the first frequency $f_1$ across a range of frequencies that span an energy level of a molecular vibrational mode of interest. When the first frequency $f_1$ corresponds to the energy level of the molecular vibrational mode, the intensity of the emitted SFG light at the third frequency $f_3$ will increase due to a resonant effect of the first light beam exciting the molecular vibrational mode. By analyzing the intensity of the detected third frequency of light $f_3$, the vibrational modes in the sample may be identified from the resonant frequencies. Furthermore, the directional dependence of the non-linear susceptibility of the sample allows a user to derive information about the orientation of molecules in the sample from the polarization of the collected SFG signal.

In one or more embodiments, the first light beam may be a spectrally broadband light beam that includes a plurality of frequencies $f_1$ while the second light beam remains at a single fixed frequency $f_2$. Accordingly, the emitted SFG light from the sample would include a plurality of third frequencies $f_3$ that may be collected simultaneously for faster data acquisition.

Figure 2:
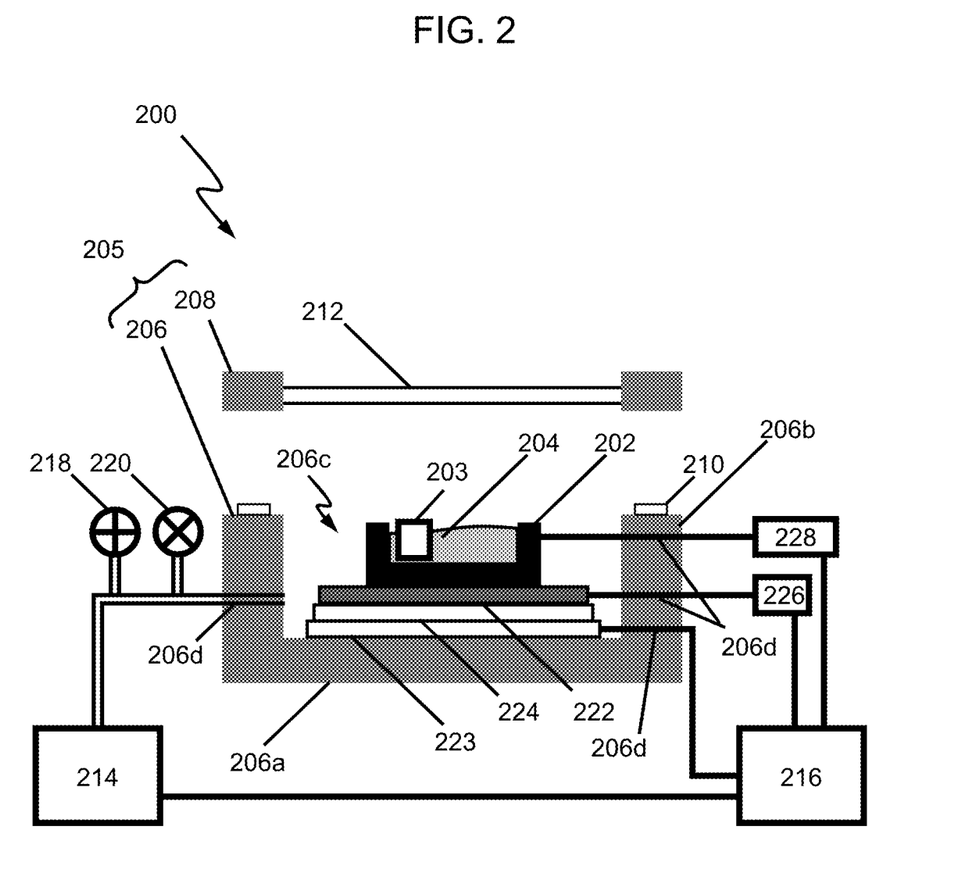
FIG. 2 shows an open pressure cell for SFG spectroscopy according to one or more embodiments.
Figure 3:
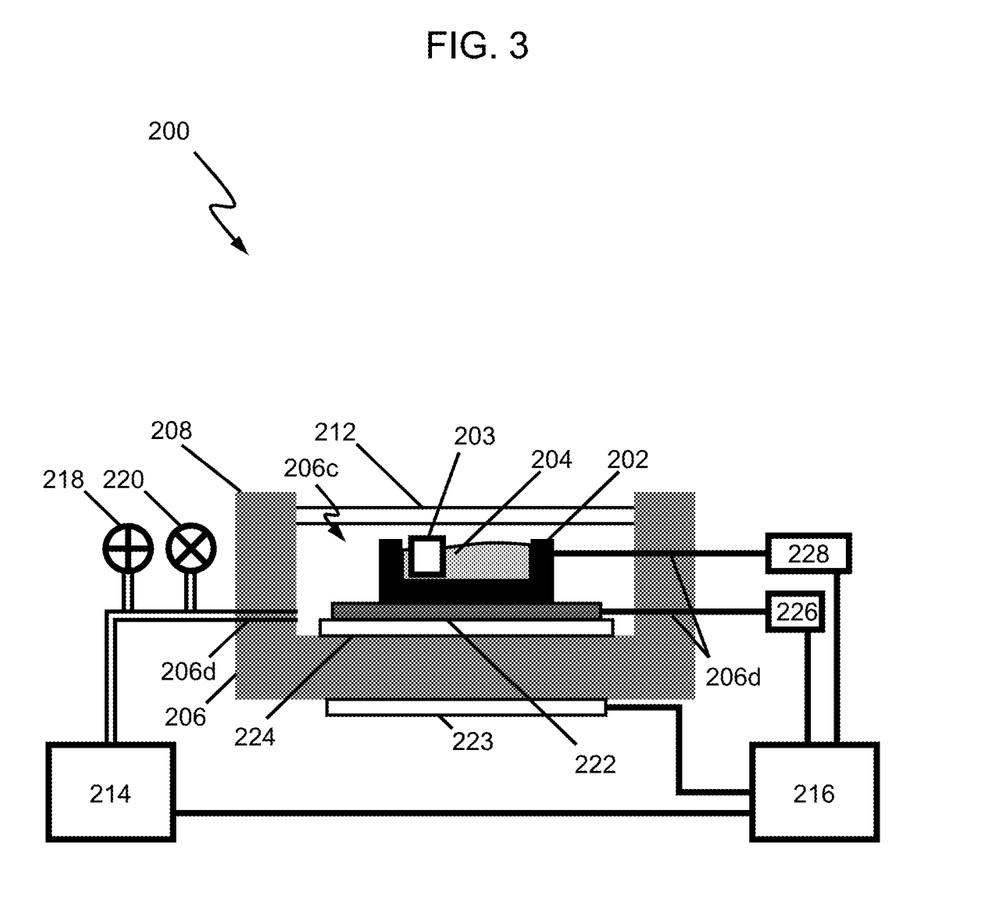
FIG. 3 shows a sealed pressure cell for SFG spectroscopy according to one or more embodiments.

FIGS. 2-3 show a pressure cell for SFG spectroscopy according to one or more embodiments. A pressure cell 200 is used to simulate the conditions that occur in the reservoir 102 (FIG. 1). The pressure cell 200 includes a metal pressure chamber 205 that retains a liquid sample 204 (e.g., a brine).

The metal pressure chamber 205 includes a base 206 and a removable lid 208. The base 206 may retain the liquid sample 204, as discussed below with respect to FIG. 6. Alternatively, a liquid sample holder 202 that is separate from the base 206, may retain the liquid sample 204, as discussed below with respect to FIGS. 2, 3, and 5. In general, the base 206 and the removable lid 208 enclose the liquid sample 204 within the metal pressure chamber 205. The base 206 and the removable lid 208 are formed from a metal and may be aluminum, stainless steel, or any other appropriate metal with sufficient strength to withstand the temperatures and pressures of a simulated reservoir environment. In one or more embodiments, the metal pressure chamber 205 may have a circular cross-section and a diameter of at least 20 cm. However, the metal pressure chamber 205 is not limited to this range of diameters and any appropriate size or shape may be used.

Figure 6:
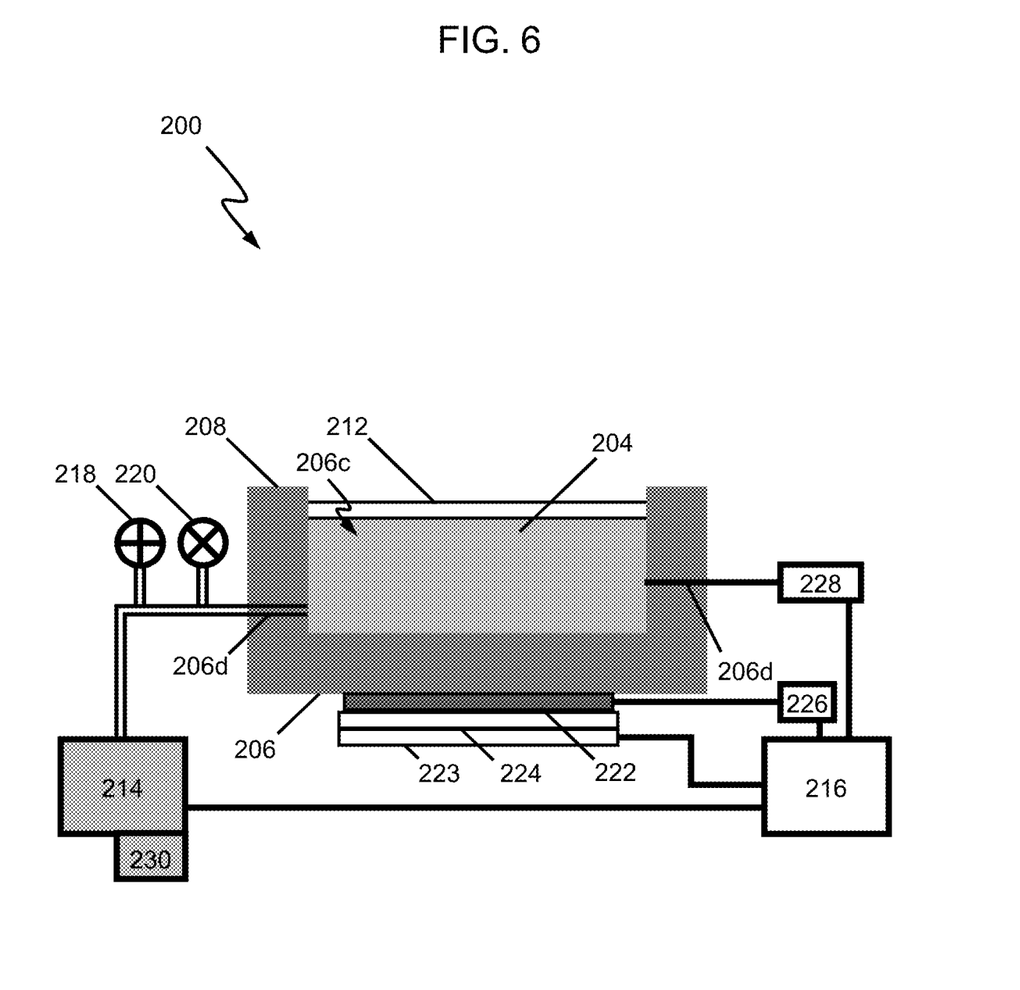
FIG. 6 shows a sealed pressure cell for SFG spectroscopy according to one or more embodiments.

As shown in FIG. 2, in one or more embodiments, the base 206 may comprise a horizontal base plate 206a and a vertical wall(s) 206b that extends in a direction perpendicular to the base plate. The base plate 206a and wall(s) 206b define a cavity 206c that retains the liquid sample 204. The base 206 includes an interior surface that is exposed to the simulated environment created inside of the pressure cell 200. The liquid sample 204 may be retained by the interior surface of the base 206, as shown in FIG. 6. Alternatively, the liquid sample holder 202 retaining the liquid sample 204 may be disposed directly or indirectly on the interior surface of the base 206. Furthermore, the base 206 includes an exterior surface that is exposed to an external environment of the metal pressure chamber 205. In one or more embodiments, the base 206 may further include one or more feedthroughs 206d that communicate between the interior surface and the exterior surface of the base 206. A feedthrough 206d may be a channel, a port, a flowline, an electrical line, an electrical conduit, an electrical plug, or any combination thereof depending on the material or signal being passed through the base 206. For example, one or more feedthroughs 206d may be electrical conduits that pass signals (e.g., control signals) or power to equipment inside the metal pressure chamber 205, as described below. In addition, one or more feedthroughs 206d may include a channel connected to a pump 214, described below, that pressurizes the interior of the metal pressure chamber 205.

The removable lid 208 cooperates with the base 206 to form the metal pressure chamber 205 that encloses the liquid sample 204. As shown in FIG. 2-3, in one or more embodiments, the removable lid 208 may be a planar plate that seals against an upper surface of the wall(s) 206b of the base 206. The removable lid 208 may attach to the base 206 by a set of cooperating threads (i.e., screws onto the base 206), one or more clips (i.e., clipped onto the base 206), or by fastening one or more fasteners (e.g., bolts, screws). However, the removable lid 208 may attach to the base 206 by any appropriate means that provides a seal to contain the pressure of the simulated reservoir environment. As shown in FIG. 2, in one or more embodiments, a seal 210 may be disposed between the base 206 and the removable lid 208 to isolate the simulated environment inside the metal pressure chamber 205 from the external environment of the metal pressure chamber 205. The seal 210 may be an elastomer O-ring, a copper gasket, any other appropriate sealing material, or any combination thereof.

In one or more embodiments, the removable lid 208 comprises a window 212 that exposes the liquid sample 204 to an exterior of the metal pressure chamber 205 (e.g., to allow external light to access the liquid sample 204). The window 212 may be transparent to a first, a second, and a third frequency of light (i.e., frequencies $f_1$, $f_2$, and $f_3$), where the third frequency $f_3$ is the sum of the first and second frequencies $f_1$, $f_2$. The window 212 may be made of glass (e.g., calcium fluoride or the like) that is transparent enough to allow the liquid sample 204 to be illuminated with light of the first and second frequencies $f_1$, $f_2$ from a source disposed outside of the metal pressure chamber 205. The window 212 may also be transparent enough to pass the generated SFG signal comprising light of the third frequency $f_3$ from the liquid sample 204 to a detector disposed outside of the metal pressure chamber 205.

In one or more embodiments, the window 212 may comprise multiple transparent windows. For example, the removable lid 208 may comprise three distinct windows 212, wherein the optical properties (e.g., transmission coefficient) of each window 212 is tuned to a corresponding first, second, and third frequency $f_1$, $f_2$, $f_3$ of light, respectively.

In general, the base 206 and the removable lid 208 cooperate to enclose the liquid sample 204 and the window 212 allows external light to access the liquid sample 204. However, other embodiments may be devised without departing from the scope of embodiments disclosed herein. For example, the base 206 may comprise only a base plate 206a while the wall(s) that define the cavity 206c of the metal pressure chamber 205 may be disposed on the removable lid 208. In this configuration, the base 206 may be removable from the lid 208. Accordingly, the one or more feedthroughs 206d may be disposed on the lid 208 rather than the base 206.

As discussed above, the metal pressure chamber 205 may include a liquid sample holder 202 that retains the liquid sample 204. The liquid sample holder 202 may be made of any appropriate material that retains the liquid sample 204. In one or more embodiments, the liquid sample holder 202 is made of a non-corrosive material (e.g., a stainless steel, a polymer, TEFLON, or the like) that can be easily cleaned of the liquid sample 204 and reused. In one or more embodiments, the liquid sample holder 202 may include a rock interface 203 (e.g., a calcite rock sample, a dolomite rock sample, an anhydrite mineral sample, a part of a carbonite rock sample, or any combination thereof) or any other appropriate material to interact with the liquid sample 204 to further simulate interactions that occur in the reservoir 102 (FIG. 1).

The liquid sample holder 202 may be any shape (e.g., circular cross-section, non-circular cross-section) provided that the liquid sample 204 retained by the liquid sample holder 202 is exposed to the interior of the metal pressure chamber 205. In one or more embodiments, the liquid sample holder 202 may be an open cylinder with a circular cross-section and a diameter of 10-15 cm. However, the liquid sample holder 202 is not limited to this range of diameters and any appropriate size or shape may be used to retain the liquid sample 204 provided the liquid sample holder 202 fits within the metal pressure chamber 205.

The pressure cell 200 further includes pump 214 that is connected to, and pressurizes, the interior of the metal pressure chamber 205. The pump 214 may be a vacuum pump, a compressor, a pneumatic compressor, a hydraulic compressor, any other appropriate mechanism that generates a pressurized environment in the interior of the metal pressure chamber 205, or any combination thereof. In one or more embodiments, the pump 214 may be vibrationally isolated from the metal pressure chamber 205 (e.g., to prevent misalignment of the incident light beams at the surface of the liquid sample 204 or to prevent loosening of the sealed connection between the base 206 and removable lid 208). For example, the feedthrough 206d and or the tubing that connects the pump 214 and the metal pressure chamber 205 may absorb mechanical vibrations from the pump 214.

The pressure range of the pump 214 may be between ambient atmospheric pressure (e.g., around 14.7 psi) to approximately 3000 psi. However, as conditions in a reservoir 102 (FIG. 1) may vary according to many parameters (e.g., depth, geographic location, rock composition), the pressure range of the pump 214 is not limited to this approximate value and pressures greater than 3000 psi may be implemented. In one or more embodiments, the pump 214 may further comprise a vacuum pump to evacuate the metal pressure chamber 205 (e.g., to outgas components).

The pump 214 may be connected to a controller 216 that provides power and control signals to the pump 214. The controller 216, described in further detail below with respect to FIG. 4, may control the pump 214 based upon a pressure gauge 218 that measures a pressure of the interior of the metal pressure chamber 205. Furthermore, the controller 216 may also control a control valve 220 that seals the metal pressure chamber 205 from the pump 214. Furthermore, the controller 216 may open the control valve 220 to release pressure from the interior of the metal pressure chamber 205. In other words, the controller 216 may control the pump 214 and the control valve 220 to control (e.g., increase, decrease, maintain) the pressure in the metal pressure chamber 205.

The pressure cell 200 further includes a heating stage 222 (e.g., a heating element) that heats the liquid sample 204. In one or more embodiments, the heating stage 222 is an electric heater (e.g., electrical joule heater, ohmic heater), however any appropriate heating element may be used to heat the liquid sample 204.

In one or more embodiments, the heating stage 222 may be disposed on an exterior surface of the metal pressure chamber 205. As discussed below with reference to FIGS. 5 and 6, the heating stage 222 may indirectly heat the liquid sample 204 by directly heating the base 206 and/or the liquid sample holder 202.

In one or more embodiments that include a liquid sample holder 202 that is separate from the base 206, the heating stage 222 may be directly connected to the liquid sample holder 202. In some embodiments, a thermal isolation layer 224 (e.g., a layer of mica, a ceramic that may include one or more of aluminum oxide ($Al_2O_3$), silica ($SiO_2$), magnesium oxide (MgO), or any combination thereof) may be disposed on the heating stage 222 (e.g., between the heating stage 222 and the metal pressure chamber 205) such that the thermal insulation layer 224 prevents the metal pressure chamber 205 from unnecessarily heating up during operation.

The temperature range of the heating stage 222 may be between 25-100 C.° to simulate the temperatures of the reservoir 102. However, as conditions in a reservoir 102 (FIG. 1) may vary according to many parameters (e.g., depth, geographic location, rock composition), the temperature range of the heating stage 222 is not limited to this range and temperatures greater than 100 C.° may be implemented.

The heating stage 222 may be connected to a temperature controller 226 disposed outside of the metal pressure chamber 205. The temperature controller 226 may be a hardware or software component of controller 216 or may be a distinct controller apparatus. The temperature controller 226 provides power and control signals to the heating stage 222 through one or more feedthroughs 206d in the metal pressure chamber 205. The temperature controller 226 may control the heating stage 222 based on a temperature of the liquid sample 204 measured by a thermocouple 228 that is connected to the interior surface of the base or the liquid sample holder 202.

In one or more embodiments, the pressure cell 200 further includes a positioning stage 223 that controls a position of a surface of the liquid sample 204. The positioning stage 223 may include one or more actuators (e.g., an electric actuator, a pneumatic actuator, a hydraulic actuator, a piezoelectric actuator, or any combination thereof) that translates the base 206 or the liquid sample holder 202 in one or more dimensions (e.g., a vertical direction) to align the surface of the liquid sample 204 with the incident light beams. The positioning stage 223 may automatically position the surface of the liquid sample 204 based on optical feedback from the surface of the liquid sample 204, as described in further detail below with respect to FIG. 7. The positioning stage 223 may be controlled by the controller 216.

In one or more embodiments, the positioning stage 223 may be disposed on an interior surface of base 206, as shown in FIG. 2. The positioning stage 223 may translate the liquid sample holder 202 and the heating stage 222 to align the surface of the liquid sample with respect to the incident light. Accordingly, the position stage 223 may be separated from the heating stage 222 by the thermal insulation layer 224 to prevent the positioning stage from unnecessarily heating up during operation.

In another embodiment, as shown in FIG. 3, the positioning stage 223 may be disposed exteriorly to the metal pressure chamber 205 while the heating stage 222 is disposed in the interior of the metal pressure chamber 205. The positioning stage 223 may translate the metal pressure chamber 205 and the entire contents thereof to align the surface of the liquid sample with respect to the incident light. An external positioning stage 223 advantageously reduces the number of feedthroughs 206d and the possibility of leaks from the metal pressure chamber 205.

Figure 4:
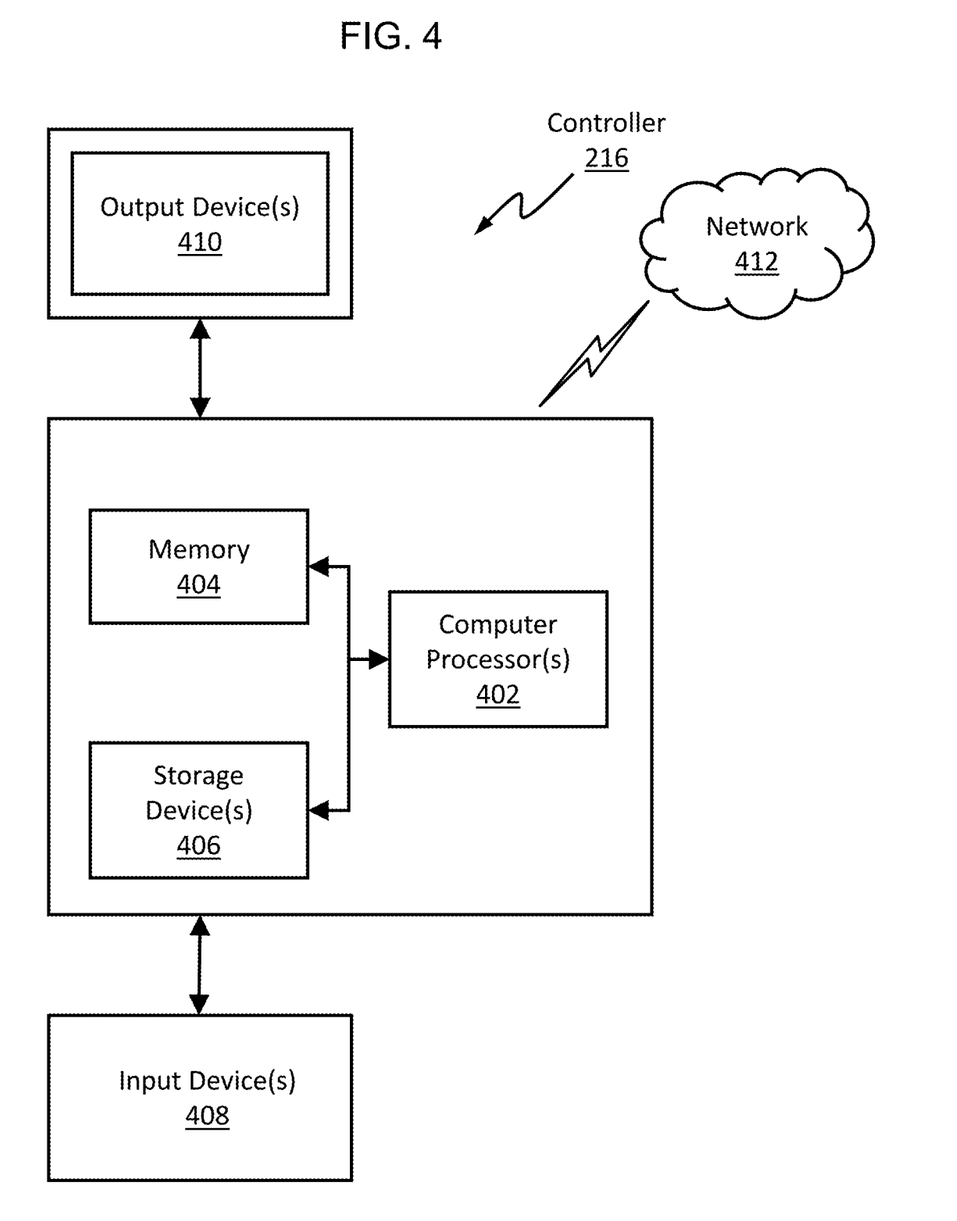
FIG. 4 shows a schematic of a controller according to one or more embodiments.

FIG. 4 shows a schematic of a controller 216 according to one or more embodiments. As discussed above, in one or more embodiments, the controller 216 may control the pump 214 and the heating stage 222 to control a pressure of the interior of the metal pressure chamber 205 and a temperature of the liquid sample 204, respectively. The controller 216 may be implemented on virtually any type of computing system, regardless of the platform being used. For example, the computing system may be one or more mobile devices (e.g., laptop computer, smart phone, personal digital assistant, tablet computer, or other mobile device), desktop computers, servers, blades in a server chassis, or any other type of computing device or devices that includes at least the minimum processing power, memory, and input and output device(s) to perform one or more embodiments disclosed herein. For example, as shown in FIG. 4 the controller 216 may include one or more computer processor(s) 402, associated memory 404 (e.g., random access memory (RAM), cache memory, flash memory), one or more storage device(s) 406 (e.g., a hard disk, an optical drive such as a compact disk (CD) drive or digital versatile disk (DVD) drive, a flash memory stick), and numerous other elements and functionalities. The computer processor(s) 402 may be an integrated circuit for processing instructions. For example, the computer processor(s) may be one or more cores, or micro-cores of a processor.

The controller 216 may also include one or more input device(s) 408, such as a pressure gauge 218, thermocouple 228, camera, imager, touchscreen, keyboard, mouse, microphone, touchpad, electronic pen, or any other type of input device. Further, the controller 216 may include one or more output device(s) 410, such as a screen (e.g., a liquid crystal display (LCD), a plasma display, touchscreen, cathode ray tube (CRT) monitor, or other display device), a printer, external storage, or any other output device. One or more of the output device(s) may be the same or different from the input device(s). The controller 216 may be connected to a network 412 (e.g., a local area network (LAN), a wide area network (WAN) such as the Internet, mobile network, or any other type of network) via a network interface connection (not shown). The input and output device(s) may be locally or remotely (e.g., via the network 412) connected to the computer processor(s) 402, memory 404, and storage device(s) 406. Many different types of computing systems exist, and the aforementioned input and output device(s) 408, 410 may take other forms.

Further, one or more elements of the controller 216 may be located at a remote location and be connected to the other elements over a network 412. Further, one or more embodiments may be implemented on a distributed system having a plurality of nodes, where each portion of the embodiment may be located on a different node within the distributed system. In one embodiment, the node corresponds to a distinct computing device. In other embodiments, the node may correspond to a computer processor with associated physical memory. In yet other embodiments, the node may correspond to a computer processor or micro-core of a computer processor with shared memory and/or resources.

Figure 5:
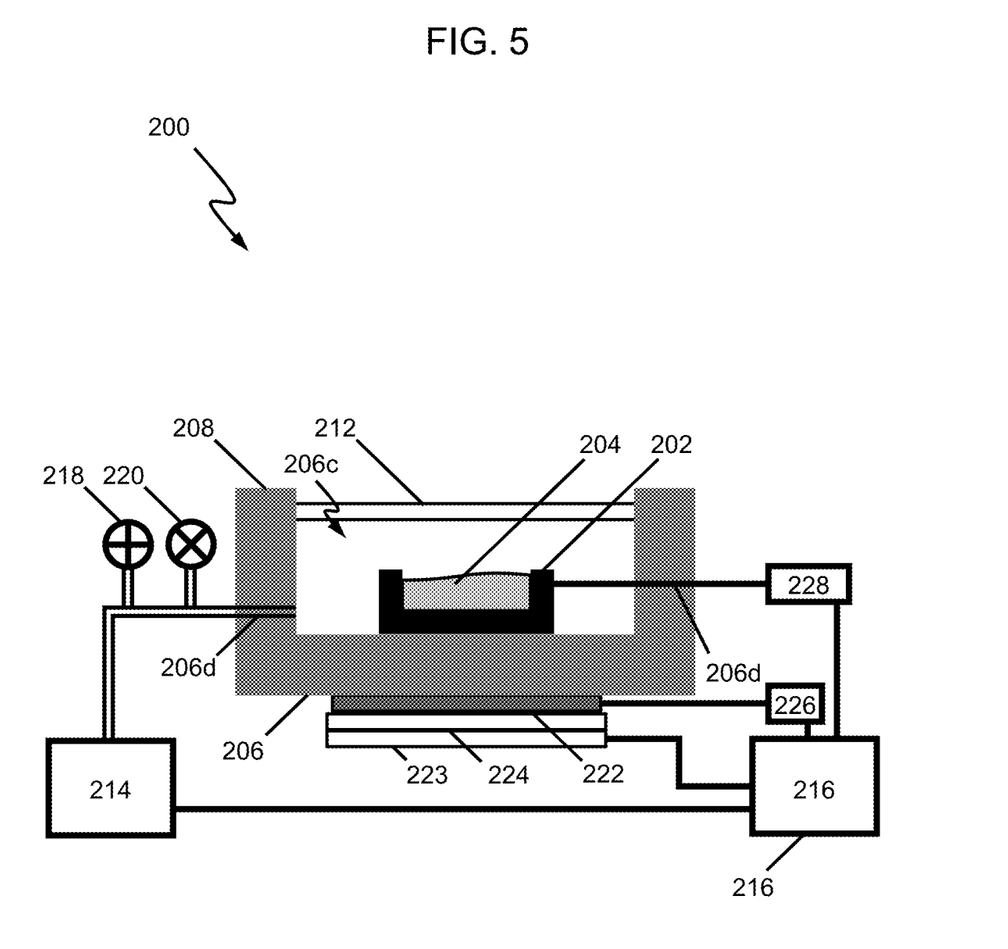
FIG. 5 shows a sealed pressure cell for SFG spectroscopy according to one or more embodiments.

FIG. 5 shows a sealed pressure cell for SFG spectroscopy according to one or more embodiments. The pressure cell 200 may be configured with the heating stage 222 disposed on an exterior surface of the base 206. For example, as shown in FIG. 5, the heating stage 222 may be disposed on the exterior surface of the base 206, and a liquid sample holder 202 may be disposed on the interior surface of the base 206. In this configuration, the heating stage 222 directly heats the base 206 and indirectly heat the liquid sample holder 202 and liquid sample 204. An external heating stage 222 advantageously reduces the number of feedthroughs 206d and the possibility of leaks from the metal pressure chamber 205.

FIG. 6 shows a sealed pressure cell 200 for SFG spectroscopy according to another embodiment in which the heating stage 222 is disposed on the exterior surface of the metal pressure chamber 205. In this configuration, an interior surface of the base 206 may constitute the liquid sample holder 202, such that a separate and distinct liquid sample holder 202 is not needed. In this configuration, the liquid sample 204 may be initially stored in a tank 230 connected to the pump 214. The pump 214 may be a hydraulic pump that injects the liquid sample 204 into the metal pressure chamber 205 from the tank 230 and pressurizes the interior of the metal pressure chamber 205 with the liquid sample 204 from tank 230. The external heating stage 222 may indirectly heat the liquid sample 204 through the base 206. The thermocouple 228 may be connected to the interior surface of the metal pressure chamber 205 to measure the temperature of the liquid sample 204.

Figure 7:
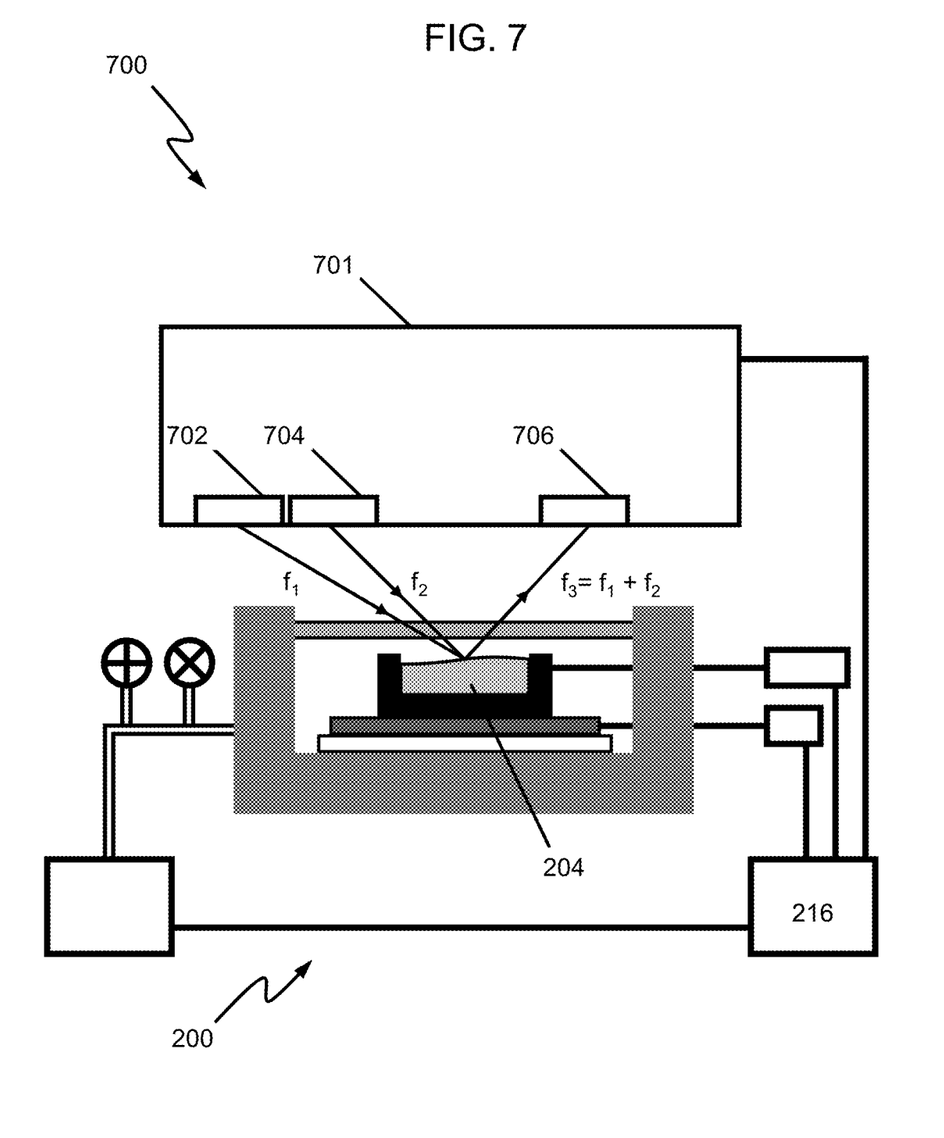
FIG. 7 shows a system for performing SFG spectroscopy according to one or more embodiments.

FIG. 7 shows a system for performing SFG spectroscopy according to one or more embodiments. A system 700 for performing SFG spectroscopy may include a pressure cell 200, as previously described with respect to the one or more embodiments of FIGS. 2-3 and 5-6, and an SFG microscope 701.

The SFG microscope 701 includes a first light source 702 that generates light of the first variable frequency $f_1$ and a second light source 704 that generates light of the second frequency $f_2$. The first variable frequency $f_1$ may correspond to the vibrational energy of a molecule in the liquid sample (e.g., corresponds to an infrared wavelength of light). The second frequency $f_2$ is different from the first frequency $f_1$ and may correspond to a virtual energy state (e.g., may correspond to a visible wavelength of light). In one or more embodiments, the first and second light sources 702, 704 are pulsed laser sources. However, the present disclosure is not limited to this configuration and any appropriate light sources for generating an SFG signal (i.e., light of the third frequency $f_3$ that is the sum of the first and second frequencies $f_1$, $f_2$) may be used. The first and second light sources 702, 704 are configured to spatially and temporally overlap the first and second light beams at the surface of the liquid sample 204 to generate the SFG signal.

The SFG microscope 701 further comprises a detector 706 that detects light. The detector 706 is offset from the light sources 702, 704 of the SFG microscope 701 to collect the SFG signal emitted from the liquid sample 204. The detector 706 may include additional optical elements (e.g., lens, spatial filter, frequency filter, spectrometer, power meter) to control, measure, and manipulate the detected light.

In one or more embodiments, the SFG microscope 701 may further include additional optical elements (e.g., mirror, lens, spatial filter, frequency filter, delay line, spectrometer, power meter) to control, measure, and manipulate the emitted and detected light.

In one or more embodiments, the SFG microscope 701 may be controlled by the controller 216. For example, the controller 216 may instruct the SFG microscope 701 to begin data acquisition once the pump 214 has pressurized the metal pressure chamber 205 to a predetermined pressure and the heating stage 222 has heated the liquid sample 204 to a predetermined temperature.

Furthermore, the controller 216 may use one or more of the first and second light sources 702, 704 to illuminate the liquid sample 204 to align the liquid sample holder 202 using the positioning stage 223. For example, a portion of the light emitted by light source 702 may reflect off of the surface of the liquid sample 204 and be detected by the detector 706 or a second detector (not shown) of the SFG microscope 701. Alternatively, the detector 706 may detect the SFG signal. Based on a position or an intensity of the detected signal, the controller 216 controls the positioning stage 223 to align the liquid sample 204 with the convergence point of the spatially and temporally overlapped first and second light beams.

Figure 8:
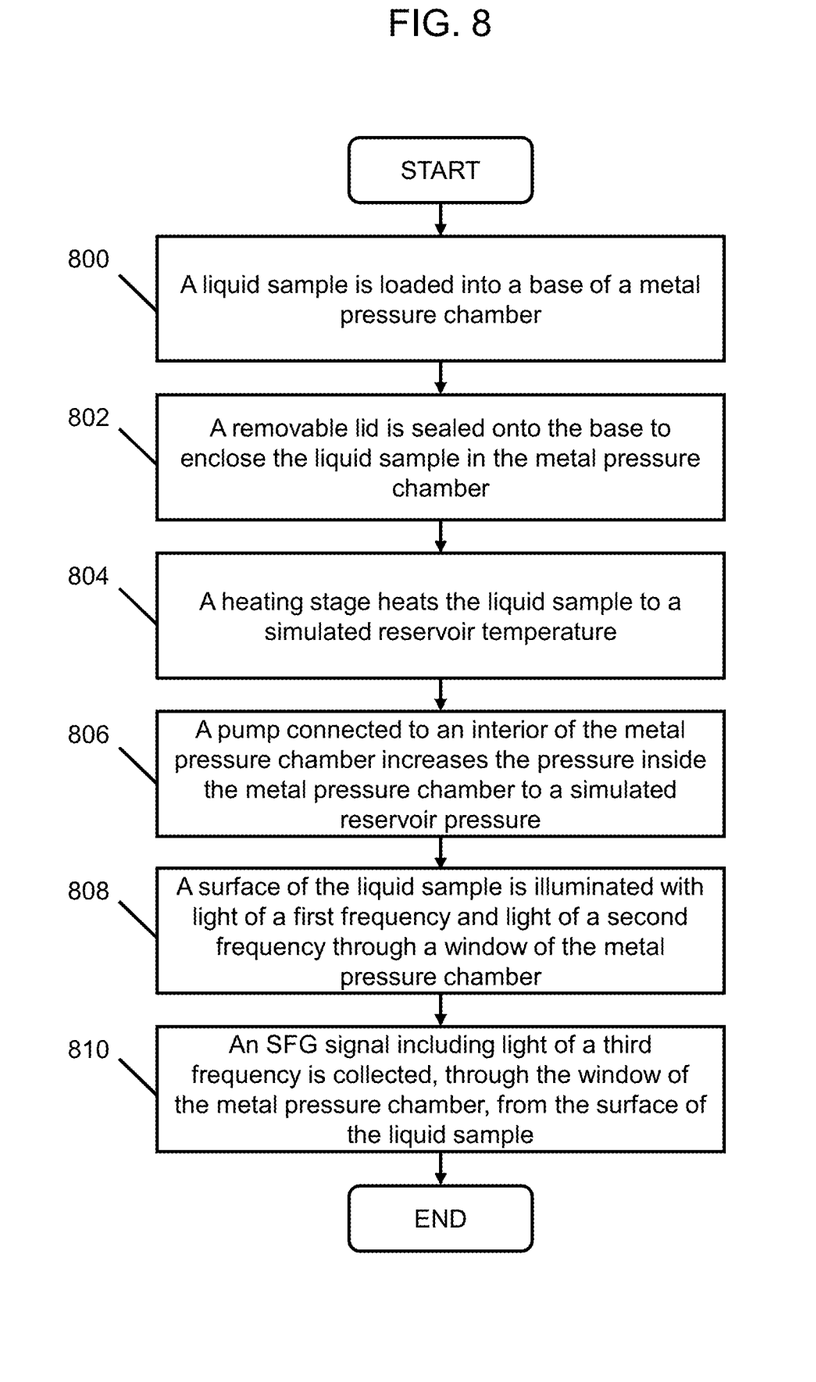
FIG. 8 shows a method for performing SFG spectroscopy according to one or more embodiments.

FIG. 8 shows a flowchart according to one or more embodiments. The flowchart depicts a method for performing SFG spectroscopy that may be performed using the pressure cell 200 described above in reference to FIGS. 2-3, 5, and 7. In one or more embodiments, one or more of the steps shown in FIG. 8 may be combined, omitted, repeated, and/or performed in a different order than the order shown in FIG. 8. Accordingly, the scope of the present disclosure should not be considered limited to the specific arrangement of steps shown in FIG. 8.

At 800, a liquid sample 204 is loaded into a base 206 of a metal pressure chamber 205. The liquid sample 204 may be a brine. In one or more embodiments, the liquid sample is loaded into a liquid sample holder 202. In one or more embodiments, the liquid sample 204 interacts with a rock interface 203 (e.g., a calcite rock sample), or any other appropriate material that may further simulate the interactions occurring in a reservoir 102, disposed within the metal pressure chamber 205.

At 802, a removable lid 208 is sealed onto the base 206 to enclose the liquid sample 204 in the metal pressure chamber 205. The seal may be formed by screwing, clipping, mechanical fastening (e.g., with bolts, screws) the removable lid 208 onto the base 206. However, the removable lid 208 may be sealed to the base 206 by any appropriate means that provides a seal to contain the pressure of the simulated reservoir environment. In one or more embodiments, a seal 210 (e.g., elastomeric O-ring, copper gasket, or other seal) may be disposed between the base 206 and the removable lid 208 to seal the metal pressure chamber 205.

At 804, a heating stage 222 heats the liquid sample 204 to a simulated reservoir temperature. In one or more embodiments, the temperature of the liquid sample 204 is raised to approximately 90-100 C°. However, as discussed above, the present disclosure is not limited to this temperature range because conditions of a reservoir 102 may vary according to many parameters (e.g., depth, geographic location, rock composition). The temperature of the liquid sample 204 may be monitored by a thermocouple 228 that is connected to the base 206 or the liquid sample holder 202. The thermocouple 228 may send temperature information to a temperature controller 226, or alternatively a controller 216, that sends power and control signals to the heating stage 222.

At 806, a pump 214 connected to an interior of the metal pressure chamber 205 increases the pressure inside the metal pressure chamber 205 to a simulated reservoir pressure. In one or more embodiments, the pressure of the liquid sample 204 is raised to approximately 3000 psi. However, as discussed above, the present disclosure is not limited to this approximate pressure value because conditions of a reservoir 102 may vary according to many parameters (e.g., depth, geographic location, rock composition). The pressure of the interior of the metal pressure chamber 205 may be monitored by a pressure gauge 218. The pressure gauge 218 may send pressure information to the controller 216 that sends power and control signals to the pump 214. Furthermore, the controller 216 may control a control valve 220 to seal the metal pressure chamber 205 from the pump 214 or release pressure from the interior of the metal pressure chamber 205.

At 808, a surface of the liquid sample 204 is illuminated with light of a first frequency $f_1$ and light of a second frequency $f_2$ through a window 212 of the metal pressure chamber 205. The incident light beams of the first and second frequencies $f_1$, $f_2$ are spatially and temporally overlapped at the surface of the liquid sample 204 to generate an SFG signal (i.e., light of the third frequency $f_3$ that is the sum of the first and second frequencies $f_1$, $f_2$).

In one or more embodiments, a positioning stage 223 may translate the surface of the liquid sample 204 to align the surface of the liquid sample 204 with the incident light beams. The positioning stage 223 may automatically position the surface of the liquid sample 204 based on a reflected signal from the surface of the liquid sample 204 (e.g., alignment with the surface of the liquid sample 204 is achieved when the reflected signal exceeds a predetermined threshold or reaches a predetermined position on a detector 706). Alternatively, the positioning stage 223 may automatically position the surface of the liquid sample 204 based on an intensity of the SFG signal (e.g., alignment with the surface of the liquid sample 204 is achieved when the SFG signal is maximized or exceeds a predetermined threshold). In yet another embodiment, the positioning stage 223 may be controlled manually.

At 810, the SFG signal, comprising the light of the third frequency $f_3$, is collected through the window 212 for analysis from the surface of the liquid sample 204.

In one or more embodiments, the heating stage 222 and the pump 214 may dynamically change the temperature and pressure inside the metal pressure chamber 205 during acquisition of the SFG signal. For example, the controller 216 may ramp the temperature or pressure to different values in response to data collected from the pressure gauge 218, the control valve 220, the thermocouple 228, the detector 706, or any combination thereof. Thus, the liquid sample 204 may be characterized in both static and dynamic reservoir environments (e.g., stable temperature and pressure conditions or dynamically changing temperature and/or pressure conditions).

In one or more embodiments, the first frequency $f_1$ may be continuously or discretely changed to obtain a spectrum of SFG signals from the liquid sample 204. In another embodiment, first frequency $f_1$ may be a spectrally broadband frequency range that includes a plurality of frequencies. Accordingly, a spectrum of SFG signals from the liquid sample 204 may be obtain at one time.

Figure 9:
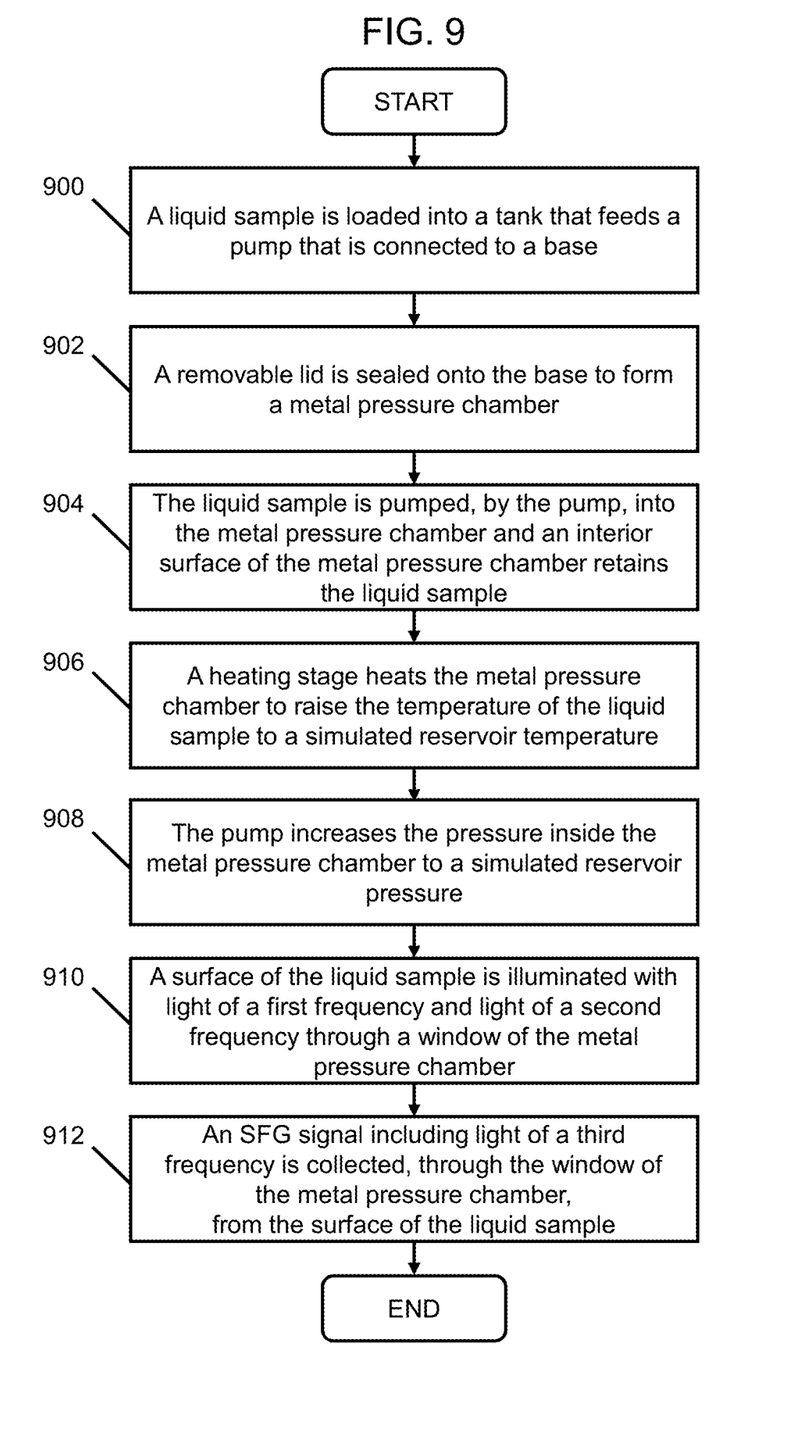
FIG. 9 shows a method for performing SFG spectroscopy according to one or more embodiments.

FIG. 9 shows a flowchart according to one or more embodiments. The flowchart depicts another method for performing SFG spectroscopy that may be performed using the pressure cell 200 described above in reference to FIG. 6. In one or more embodiments, one or more of the steps shown in FIG. 9 may be combined, omitted, repeated, and/or performed in a different order than the order shown in FIG. 9. Accordingly, the scope of the present disclosure should not be considered limited to the specific arrangement of steps shown in FIG. 9.

At 900, a liquid sample 204 is loaded into a tank 230 that feeds a pump 214 connected to a base 206. The liquid sample 204 may be a brine.

At 902, a removable lid 208 is sealed onto the base 206 to form a metal pressure chamber 205. The seal may be formed by screwing, clipping, fastening (e.g., with bolts, screws) the removable lid 208 onto the base 206. However, the removable lid 208 may be sealed to the base 206 by any appropriate means that provides a seal to contain the pressure of the simulated reservoir environment. In one or more embodiments, a seal 210 (e.g., elastomeric O-ring, copper gasket) may be disposed between the base 206 and the removable lid 208 to seal the metal pressure chamber 205.

At 904, the liquid sample 204 is pumped, by the pump 214, into the metal pressure chamber 205 and the interior surface of the base 206 retains the liquid sample 204. In one or more embodiments, a rock interface 203 (e.g., a calcite rock sample), or any other appropriate material that may further simulate interactions occurring in a reservoir 102, is disposed in the metal pressure chamber to interact with the liquid sample 204.

At 906, a heating stage 222 heats the metal pressure chamber 205 to raise temperature of the liquid sample 204 to a simulated reservoir temperature. In one or more embodiments, the temperature of the liquid sample 204 is raised to approximately 90-100 C°. However, as discussed above, the present disclosure is not limited to this temperature range because conditions of a reservoir 102 may vary according to many parameters (e.g., depth, geographic location, rock composition). The temperature of the liquid sample 204 may be monitored by a thermocouple 228 that is connected to the internal surface of the base 206. The thermocouple 228 may send temperature information to a temperature controller 226, or alternatively a controller 216, that sends power and control signals to the heating stage 222.

At 908, the pump 214 increases the pressure inside the metal pressure chamber 205 to a simulated reservoir pressure. In one or more embodiments, the pressure of the liquid sample 204 is raised to approximately 3000 psi. However, as discussed above, the present disclosure is not limited to this approximate pressure value because conditions of a reservoir 102 may vary according to many parameters (e.g., depth, geographic location, rock composition). The pressure of the interior of the metal pressure chamber 205 may be monitored by a pressure gauge 218. The pressure gauge 218 may send pressure information to the controller 216 that sends power and control signals to the pump 214. Furthermore, the controller 216 may control a control valve 220 to seal the metal pressure chamber 205 from the pump 214 or release pressure from the metal pressure chamber.

At 910, a surface of the liquid sample 204 is illuminated with light of a first frequency $f_1$ and light of a second frequency $f_2$ through a window 212 of the metal pressure chamber 205. The incident light beams of the first and second frequencies $f_1$, $f_2$ are spatially and temporally overlapped at the surface of the liquid sample 204 to generate an SFG signal (i.e., light of the third frequency $f_3$ that is the sum of the first and second frequencies $f_1$, $f_2$).

In one or more embodiments, a positioning stage 223 may translate the metal pressure chamber 205 to align the surface of the liquid sample 204 with the incident light beams. The positioning stage 223 may automatically position the surface of the liquid sample 204 based on a reflected signal from the surface of the liquid sample 204 (e.g., alignment with the sample surface is achieved when the reflected signal exceeds a predetermined threshold or reaches a predetermined position on a detector 706). Alternatively, the positioning stage 223 may position the surface of the liquid sample 204 based on an intensity of the SFG signal (e.g., alignment with the sample surface is achieved when the SFG signal is maximized or exceeds a predetermined threshold). In yet another embodiment, the positioning stage 223 may be controlled manually.

At 912, the SFG signal, comprising the light of the third frequency $f_3$, is collected through the window 212 for analysis from the surface of the liquid sample 204.

In one or more embodiments, the heating stage 222 and the pump 214 may dynamically control the temperature and pressure inside the metal pressure chamber 205 during acquisition of the SFG signal. For example, the controller 216 may ramp the temperature or pressure to different values such that the liquid sample 204 may be characterized in both static and dynamic reservoir environments (e.g., stable temperature and pressure conditions or dynamically changing temperature and/or pressure conditions).

In one or more embodiments, the first frequency $f_1$ may be continuously or discretely changed to obtain a spectrum of SFG signals from the liquid sample 204. In another embodiment, first frequency $f_1$ may be a spectrally broadband frequency range that includes a plurality of frequencies. Accordingly, a spectrum of SFG signals from the liquid sample 204 may be obtain at one time.

Software instructions in the form of computer readable program code to perform embodiments of the present disclosure may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that when executed by a processor(s), is configured to perform embodiments disclosed herein.

One or more of the embodiments disclosed herein may have one or more of the following advantages and improvements over conventional SFG spectroscopy techniques: simulating reservoir conditions (e.g., high pressure, high temperature environments); simulating reservoir interactions for study in a controlled environment; SFG spectroscopy under static and dynamic temperature and/or pressure conditions; simplifying analysis of hydrocarbon samples compared to downhole measurements; and improving the accuracy of experiments analyzing liquid/liquid and liquid/solid interfaces under reservoir conditions. One or more of the above advantages may improve a user's understanding of the chemical and molecular structures and interfaces that occur in a reservoir and improve the effectiveness of hydrocarbon recovery techniques.

Although the disclosure has been described with respect to only a limited number of embodiments, those skilled in the art, having benefit of this disclosure, will appreciate that various other embodiments may be devised without departing from the scope of the present disclosure. Accordingly, the scope of the disclosure should be limited only by the attached claims.

What is claimed:

1. A pressure cell for sum frequency generation spectroscopy, the pressure cell comprising:
    a metal pressure chamber comprising:
        a base;
        a thermal insulation layer disposed on an interior surface of the base;
        a liquid sample holder, disposed within the base, to retain a liquid sample;
        a heating stage disposed between the thermal insulation layer and the liquid sample holder to heat the liquid sample;
        a removable lid that seals against the base to enclose the liquid sample in the metal pressure chamber; and
        a window in the removable lid that exposes the liquid sample to an exterior of the metal pressure chamber;
    a pump, fluidly connected to an interior of the metal pressure chamber, that pressurizes the interior of the metal pressure chamber; and
    a controller that controls the pump and the heating stage to control a pressure of the interior of the metal pressure chamber and a temperature of the liquid sample.

2. The pressure cell according to claim 1, wherein the pump is a liquid pump that pressurizes the interior of the metal pressure chamber with the liquid sample.

3. The pressure cell according to claim 1, further comprising:
    a pressure gauge that measures the pressure of the interior of the metal pressure chamber; and
    a control valve that seals the metal pressure chamber from the pump, wherein
    the controller controls the pump and the control valve to control the pressure of the interior of the metal pressure chamber.

4. The pressure cell according to claim 1, wherein the metal pressure chamber encloses a rock interface that interacts with the liquid sample.

5. The pressure cell according to claim 1, further comprising:
    a thermocouple that measures the temperature of the liquid sample; and
    a temperature controller that controls the heating stage.

6. The pressure cell according to claim 1, further comprising a positioning stage that controls a position of a surface of the liquid sample.

7. A system for sum frequency generation spectroscopy, the system comprising:
    a pressure cell comprising:
        a metal pressure chamber including:
            a base;
            a thermal insulation layer disposed on an interior surface of the base;
            a liquid sample holder, disposed within the base, to retain a liquid sample;
            heating stage disposed between the thermal insulation layer and the liquid sample holder to heat a liquid sample;
            a removable lid that seals against the base to enclose the liquid sample in the metal pressure chamber; and
            a window in the removable lid that exposes the liquid sample to an exterior of the metal pressure chamber;
        a pump, fluidly connected to an interior of the pressure chamber, that pressurizes the interior of the metal pressure chamber; and
        a controller that controls the pump and the heating stage to control a pressure of the interior of the metal pressure chamber and a temperature of the liquid sample; and
    a sum frequency generation microscope comprising:
        a first variable light source that generates light of a first frequency;
        a second light source that generates light of a second frequency;
        and a detector that detects light.

8. The system according to claim 7, wherein the pump is a liquid pump that pressurizes the interior of the metal pressure chamber with the liquid sample.

9. The system according to claim 7, wherein the pressure cell further comprises:
   a pressure gauge that measures the pressure of the interior of the metal pressure chamber; and
   a control valve that seals the metal pressure chamber from the pump, wherein
      the controller controls the pump and the control valve to control the pressure of the interior of the metal pressure chamber.

10. The system according to claim 7, wherein the metal pressure chamber encloses a rock interface that interacts with the liquid sample.

11. A method of performing sum frequency generation spectroscopy in a pressure cell, the method comprising:
   loading a liquid sample into a liquid sample holder;
   loading the liquid sample holder into a metal pressure chamber of the pressure cell, wherein the metal pressure chamber comprises a base, a thermal insulation layer disposed on an interior surface of the base, a heating stage disposed between the thermal insulation layer and the liquid sample holder, and a removeable lid;
   sealing the removable lid against the base to enclose the liquid sample in the metal pressure chamber;
   heating the liquid sample with the heating stage;
   pressurizing an interior of the metal pressure chamber with a pump fluidly connected to the interior of the metal pressure chamber;
   illuminating a surface of the liquid sample with light of a first frequency and light of a second frequency through a window of the metal pressure chamber; and
   collecting, through the window, light of a third frequency from the surface of the liquid sample, wherein the third frequency is the sum of the first frequency and the second frequency.

12. The method according to claim 11, wherein
   the pump is a liquid pump, and
   pressurizing the interior of the metal pressure chamber comprises pumping the liquid sample, with the liquid pump, into the interior of the metal pressure chamber until a predetermined internal pressure is reached.

13. The method according to claim 11, further comprising:
   measuring a pressure of the interior of the metal pressure chamber with a pressure gauge; and
   sealing the metal pressure chamber from the pump with a control valve; and
   controlling the pressure of the interior of the metal pressure chamber with the pump and the control valve based on the pressure measured by the pressure gauge.

14. The method according to claim 11, further comprising disposing, within the metal pressure chamber, a rock interface that interacts with the liquid sample.

* * * * *